United States Patent

Scherl

[11] Patent Number: 6,155,987
[45] Date of Patent: Dec. 5, 2000

[54] ASSEMBLY FOR REMOVING EAR WAX FROM ONE'S EAR CANAL

[76] Inventor: Michael Scherl, 257 N. Woodland St., Englewood, N.J. 07631

[21] Appl. No.: 09/404,252

[22] Filed: Sep. 22, 1999

Related U.S. Application Data

[60] Provisional application No. 60/119,426, Feb. 11, 1999.

[51] Int. Cl.[7] .................................................. A61B 10/00
[52] U.S. Cl. ........................ 600/562; 128/898; 604/317; 606/162
[58] Field of Search .................................. 600/562, 570, 600/200; 604/264, 317, 327, 346; 606/108, 162; 128/898

[56] References Cited

U.S. PATENT DOCUMENTS

| | | | |
|---|---|---|---|
| 3,651,808 | 3/1972 | White | 604/213 |
| 4,201,212 | 5/1980 | Bradley | 604/346 |
| 4,441,485 | 4/1984 | Reynolds | 600/200 |
| 4,993,406 | 2/1991 | Reynolds | 600/200 |
| 5,395,357 | 3/1995 | Weigel | 604/346 |
| 5,674,196 | 10/1997 | Donaldson et al. | 604/93.01 |
| 5,715,850 | 2/1998 | Markgraaf | 132/333 |
| 5,888,199 | 3/1999 | Karell et al. | 606/162 |
| 5,916,150 | 6/1999 | Sillman | 600/184 |
| 5,961,441 | 10/1999 | Plumb et al. | 600/20 |

*Primary Examiner*—Cary O'Connor
*Assistant Examiner*—Charles Marmor, II
*Attorney, Agent, or Firm*—William W. Jones

[57] ABSTRACT

An ear wax-removal assembly includes a funnel-shaped speculum that is inserted into a patient's ear canal, and an ear wax repository which is articulated to the speculum. The repository can take the form of a cavity, a sheet, or a suction mechanism. In each case, the position of the speculum governs the position of the repository, and both are controlled by a physician during the ear wax removal procedure. The assembly eliminates the use of a separate gauze sheet for removal of dislodged ear wax from the cleaning tool, which gauze sheet is typically placed on the shoulder of the patient; and the assembly also eliminates the need for an attendant for cleaning dislodged ear wax from the cleaning tool.

23 Claims, 5 Drawing Sheets

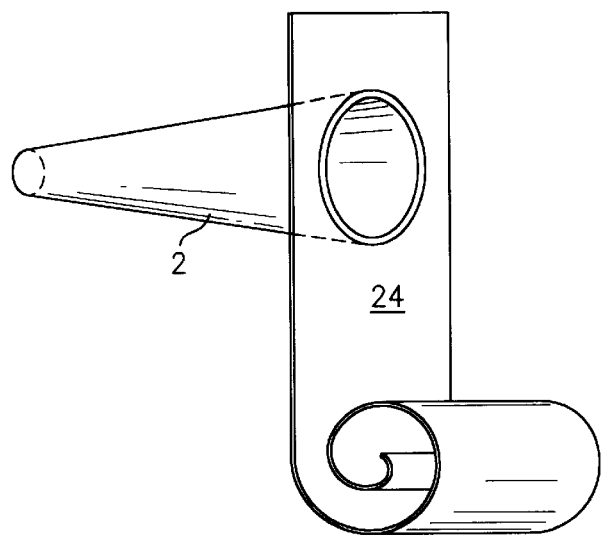
FIG. 7
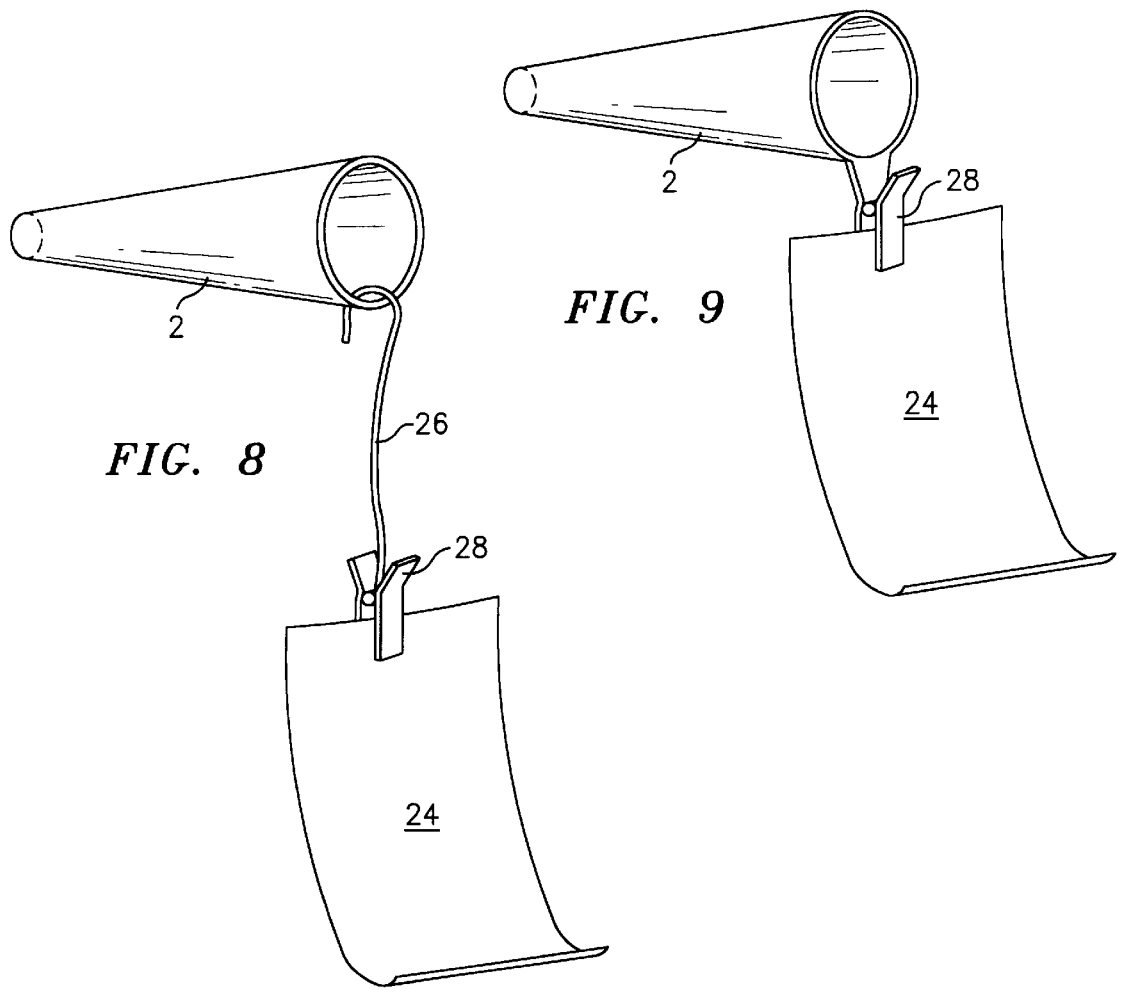
FIG. 8
FIG. 9

ASSEMBLY FOR REMOVING EAR WAX FROM ONE'S EAR CANAL

This application claims the benefit of the filing date of co-pending provisional patent application U.S. Ser. No. 60/119,426, filed Feb. 11, 1999.

TECHNICAL FIELD

This invention relates to an assembly for removing ear wax from a patient's ear canal. More particularly, this invention relates to an ear wax removal assembly which includes an ear wax repository which is either integral with or attached to a funnel portion of the assembly.

BACKGROUND ART

Ear wax, or cerumen, buildup in the ear canal can adversely effect one's hearing, and thus the ear wax will be periodically removed from the ear canal by a physician, typically an Otolaryngologist. Typically, during the removal procedure, the Otolaryngologist wears a headlamp or mirror and uses one hand to stabilize a funnel-shaped speculum and the other hand to maneuver a curette or suction to coax the wax out of the ear canal via the speculum. Each pass of the curette or suction will result in removal of only a portion of the wax, which the physician must discard before making another pass with the tool. The wax is typically removed from the tool by wiping the wax off of the tool and onto a gauze or other repository sheet that is draped over the patient's shoulder by the physician. Alternatively, an assistant may be employed to stand by the patient and wipe the wax off of the tool onto a gauze sheet which is held by the assistant. In the first instance, the gauze repository placed on the patient's shoulder is vulnerable to falling off of the shoulder, forcing the physician to re-position the gauze on the shoulder thereby interrupting the wax removal procedure. This may occur several times during the procedure. In the second case, the expense of the procedure is increased due to the use of an assistant to the physician, who is merely employed to remove wax from the tool so that the physician can continue the cleaning process with a clean tool. It is thus apparent that the presently utilized procedure for removal of excess wax from one's ears has certain inherent drawbacks. It would be highly desirable to provide a system and method for the removal of excess ear wax from the ear canal which would not entail the placement of a gauze repository on the patient's shoulder, and would not require the use of an assistant for cleaning the wax-removal tool for the physician.

DISCLOSURE OF THE INVENTION

This invention relates to an improved method and paraphernalia for use by a physician during the removal of excess cerumen from a patient's ear canal. The invention involves the use of a funnel-shaped speculum which has an ear wax repository that is either attached to the speculum, integral with the speculum, or otherwise rendered closely proximate to the speculum. The repository can take the form of an absorbent sheet, such as gauze, or it can take the form of a cavity into which the excess wax is scraped off of the removal tool, The cavity can be disposed on a component that is associated with the speculum in any of a number of different ways, as will be described hereinafter, or the cavity can be formed as an integral part of the speculum. The speculum and/or the cavity can be formed from a discardable material, or they can be formed from a reusable material.

In one embodiment of the invention, the member which includes the wax repository cavity is configured so as to be able to be suspended from the patient's ear during the wax removal procedure. This embodiment will be provided with an opening through which the speculum can be inserted into the ear canal. In another embodiment of the invention, the member which includes the wax repository cavity can be held in place by engagement thereof with the speculum. With this embodiment, the physician controls the position of the wax repository cavity simply by holding the speculum. In still another embodiment of the invention, the wax repository cavity is formed integral with the speculum so that positioning of the speculum results in like positioning of the wax repository cavity.

The wax repository cavity can be uniquely configured so as to assist in more complete removal of ear wax from the cleaning tool. For example, the rim of the wax repository cavity can be notched or serrated so that the tip of the tool can be inserted into a clean notch or serration and drawn backward out of the notch or serration thereby scraping the wax onto the sides of the notches or serrations.

It is therefore an object of this invention to provide an apparatus and method for use in removing excess ear wax from a patient's ear canal.

It is a further object of this invention to provide an apparatus and method of the character described which includes an ear wax repository component that is closely associated with an ear canal speculum that is held by the physician during the cleaning procedure.

It is yet another object of this invention to provide an apparatus and method of the character described wherein the physician controls the position of the ear wax repository component by controlling the position of the ear canal speculum.

It is an additional object of this invention to provide an apparatus and method of the character described wherein the ear wax repository component is a cavity into which ear wax can be scraped from a cleaning tool.

It is yet another object of this invention to provide an apparatus and method of the character described wherein the ear wax repository component is a sheet of material onto which the ear wax can be wiped from the cleaning tool.

BRIEF DESCRIPTION OF THE DRAWINGS

These and other objects and advantages of the invention will become more readily apparent from the following detailed description of several embodiments of the invention when taken in conjunction with the accompanying drawings in which:

FIG. 7 is a perspective view of a ear wax removal speculum assembly formed in accordance with this invention which includes a gauze, cloth or paper ear wax repository component which is mounted directly on the speculum;

FIG. 8 is a perspective view of a ear wax removal speculum assembly formed in accordance with this invention which includes a gauze, cloth or paper ear wax repository component which is connected to the speculum by means of a hook and clip;

FIG. 9 is a perspective view of a ear wax removal speculum assembly formed in accordance with this invention which includes a gauze, cloth or paper ear wax repository component which is connected to the speculum by means of a clip;

DETAILED DESCRIPTION OF SPECIFIC EMBODIMENTS OF THE INVENTION

Figure 1:
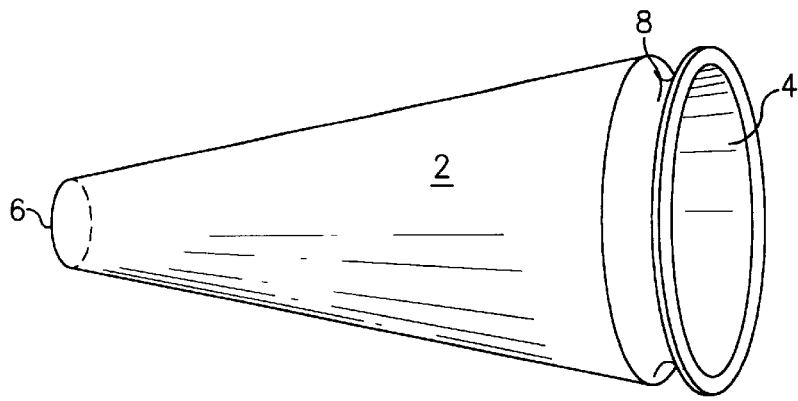
FIG. 1 is a perspective view of an ear wax speculum assembly component formed in accordance with this invention.
Figure 2:
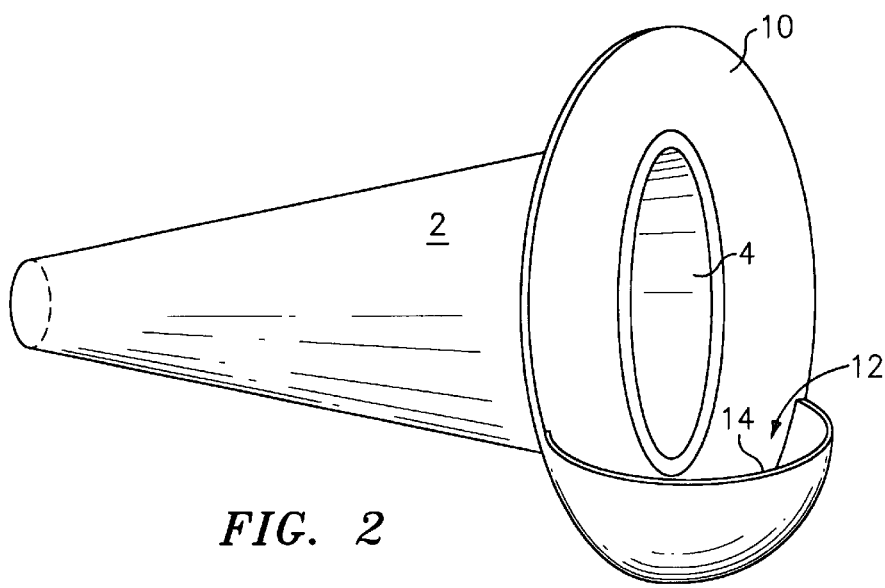
FIG. 2 is a perspective view the the component of FIG. 1 fitted with an ear wax repository cavity collar in accordance with this invention.
Figure 3:
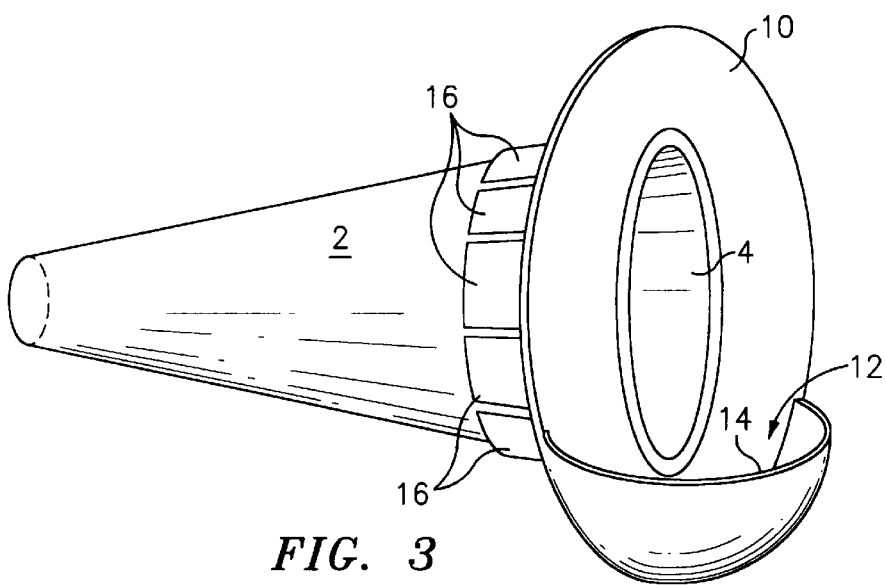
FIG. 3 is a perspective view similar to FIG. 2, but showing a variation of the ear wax collection cavity collar fitted onto the speculum.

Referring now to the drawings, there is shown in FIGS. 1–3, first embodiments of an ear wax removal speculum denoted generally by the numeral 2, which is generally funnel-shaped, with a larger end 4 and an opposite smaller end 6. It will be understood that an ear canal-cleaning tool, such as a curette, or the like, is inserted into the ear canal through the speculum 2. The speculum 2 is formed with an annular groove 8 adjacent to the larger end 4 thereof. As seen in FIGS. 2 and 3, the speculum 2 has a wax repository cavity collar 10 fitted onto the speculum 2 adjacent to the larger end 4 thereof. The collar 10 has an ear wax repository cavity 12 formed on a portion of the speculum which is closely adjacent to the larger end 4 of the speculum 2. The location of the cavity 12 allows the physician to withdraw the ear canal cleaning tool from the speculum 2 and scrape the waxy tip of the tool on the rim 14 of the cavity 12, thereby scraping ear wax off of the tool and depositing the ear wax in the cavity 12. The collar 10 can be pushed onto the speculum 2 from the smaller end 6 thereof, until the collar 10 snaps into the groove 8. In the embodiment of the device shown in FIG. 3, the collar 10 is provided with dependent spring fingers 16 which are operable to grip the outer surface of the speculum 2 as the collar 10 is pushed onto the speculum 2. In this embodiment of the invention, the groove 8 on the speculum 2 can be omitted. Alternatively, it will be readily appreciated that the collar 10 could be formed as an integral part of the speculum 2. In the embodiments shown in FIGS. 1–3, the speculum 2 and the collar 10 can be made from single use disposable materials; or simply the collar 10 could be made from single use disposable materials; or both components 2 and 10 could be made from reusable materials.

Figure 4:
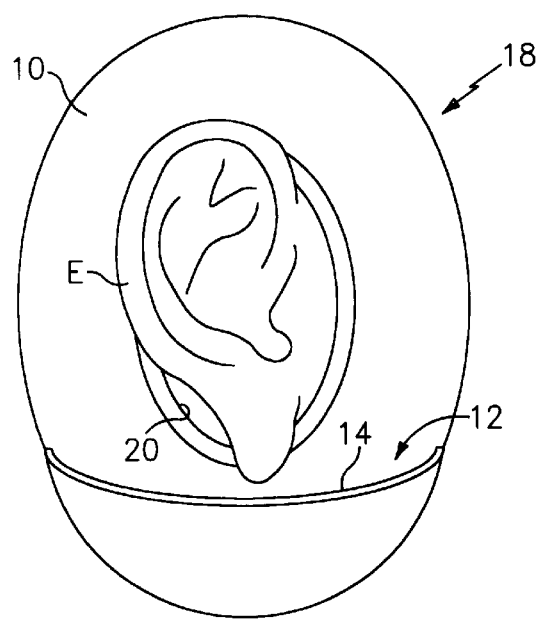
FIG. 4 is an elevational view of an embodiment of the invention which can be suspended on the ear during the ear wax removal procedure.
Figure 5:
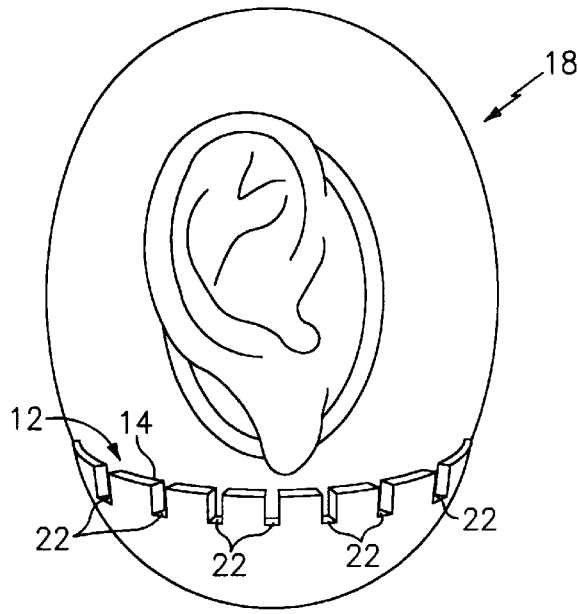
FIG. 5 is a fragmented elevational view similar to FIG. 4, but, showing a form of the assembly of FIG. 4 wherein the ear wax repository cavity includes a notched rim for assistance in cleaning the tip of the ear canal cleaning tool.
Figure 6:
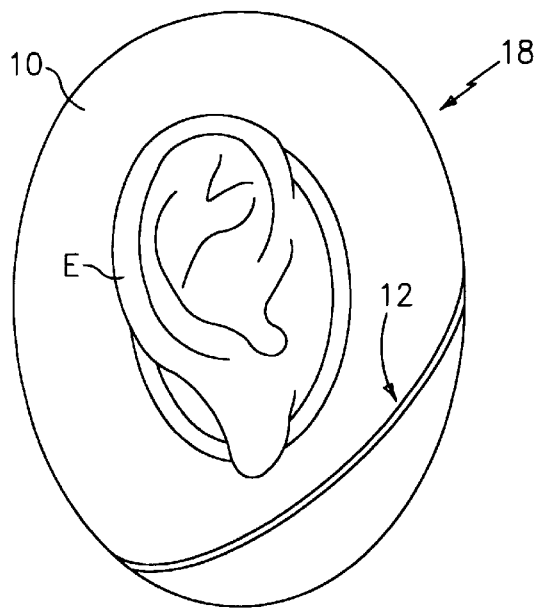
FIG. 6 is an elevational view similar to FIG. 4, but showing yet another alternative embodiment of the speculum assembly of this invention.

FIGS. 4–6 illustrate details of another embodiment 18 of the ear canal wax removal assembly which can be suspended from the patient's ear during use. The device 18 includes a larger collar 10 which has an opening 20 that is sized so as to be able to receive the patient's ear E whereby the collar 10 can be suspended from the patient's ear during the ear canal cleaning procedure. The collar 10 is provided with the ear wax repository cavity 12 and the tool scraping rim 14. In the embodiment if the device 18 shown in FIG. 5, the ear wax repository cavity rim 14 is provided with a plurality of notches 22 through which the waxy end of the wax removal tool can be drawn so as to scrape wax off of the tool. It is noted that the provision of a plurality of notches 22 on the rim 14 ensures the supply of a plurality of clean wax-removal locations in the cavity 12. In the embodiment of the device 18 shown in FIG. 6, the cavity 12 is located to one side of the collar 10, which may be to either side, depending on the handedness of the physician using the device.

FIGS. 7–9 illustrate an alternative embodiment of the ear wax removal assembly of this invention. In the alternative embodiment of the assembly, a strip 24 of an ear wax absorbent repository material is removably connected to the speculum 2. The strip 24 is connected directly to the speculum 2 in the embodiment shown in FIG. 7. When the strip 24 is connected directly to the speculum 2, as shown in FIG. 7, the opening in the strip 24 which receives the speculum 2 may be reinforced so as to prevent the strip 24 from tearing away from the speculum 2. In the embodiment shown in FIG. 8, the strip 24 is connected to the speculum 2 by means of a releasable hook 26 and a releasable clip 28. In the embodiment shown in FIG. 9, the strip 24 is connected to the speculum 2 merely by means of the releasable clip 28. In each of the embodiments shown in FIGS. 7–9, the location of the strip 24 is directly controlled by the position of the speculum 2.

Figure 10:
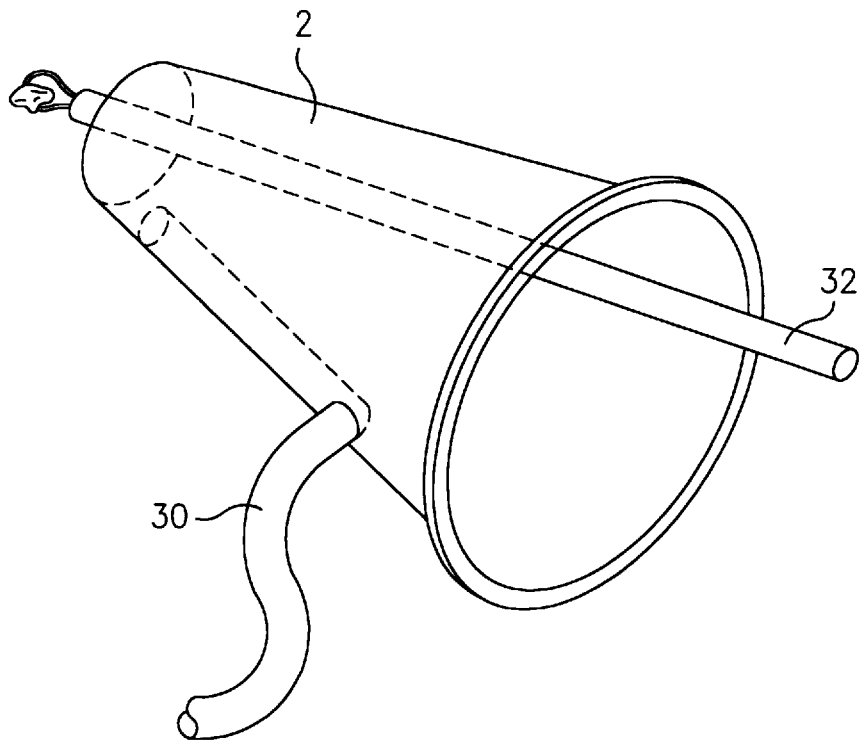
FIG. 10 is a perspective view of an ear wax removal speculum assembly that includes ear irrigation and ear suction adjuncts.
Figure 11:
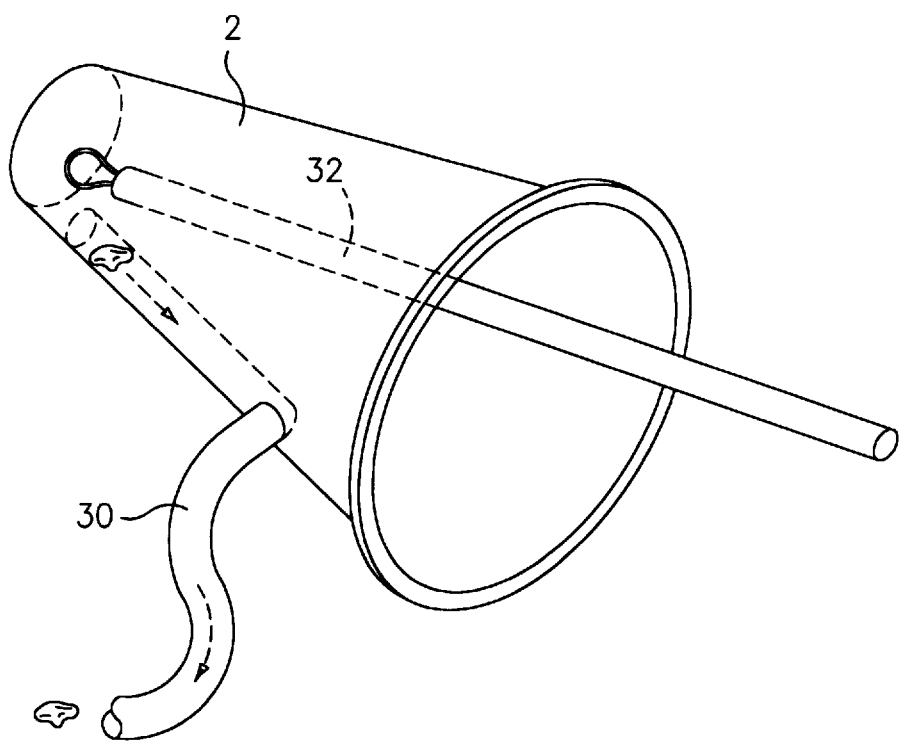
FIG. 11 is a perspective view of the ear wax removal speculum assembly of FIG. 10, but seen from the inner end of the speculum assembly.

Referring now to FIGS. 10 and 11, there is shown yet another embodiment of the ear wax removal speculum 2 of this invention which may include an ear canal suction tube 30 which is connected to an interior wall of the speculum 2. The suction tube 30 is used in conjunction with an ear wax removal tool 32 such as a curette. The ear canal is cleansed of ear wax by the tool 32 and tool 32 is then brought in close contact with the inner end of the suction tube 30, whereupon ear wax globules W are drawn off of the tool 32 and sucked into the tube 30.

Figure 12:
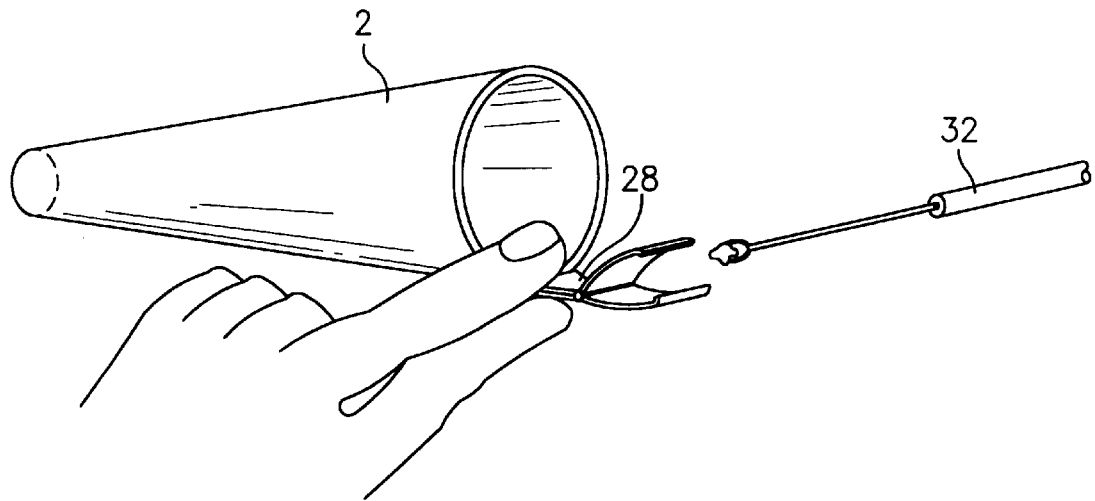
FIGS. 12 and 13 are perspective views of an ear wax removal speculum assembly wherein the ear wax receptor is a spring clip that is attached to the speculum.
Figure 13:
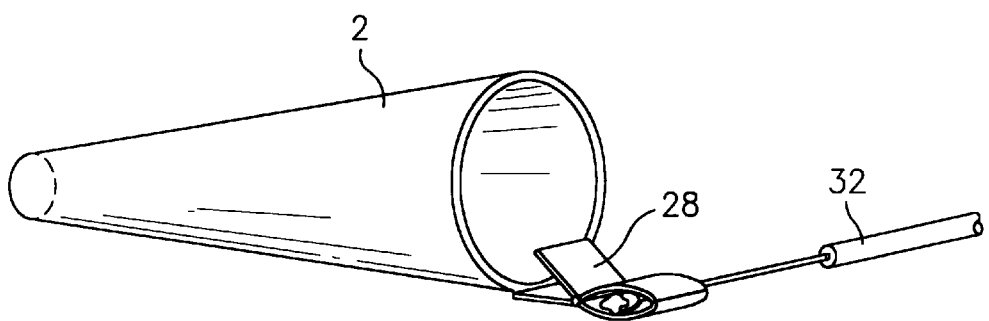

Referring now to FIGS. 12 and 13, there is shown an embodiment of the speculum 2 of this invention wherein a clip 28 that is attached to the speculum 2 is used as a receptor for ear wax from the tool 32. The clip 28 can be opened by the physician, as shown in FIG. 12, the waxy end of the tool 32 inserted into the open clip 28, and the clip 28 can then be closed to capture the wax on the tool 32. When the tool 32 is withdrawn from the closed clip 28, the wax will remain behind inside of the clip 28. The physician's hand that holds the speculum 2 can easily manipulate the clip 28.

It will be appreciated that use of the ear wax removal assembly of this invention negates the need to place an auxiliary gauze sheet on the shoulder of the patient, and also negates the necessity of employing an assistant who cleans the ear wax removal tools. The ear wax repository portion of the assembly can be formed from single use disposable materials such as plastic, paper, or the like, or it can be formed from metal which provides a reusable assembly that can be cleaned and sterilized between uses.

Since many changes and variations of the disclosed embodiments of the invention may be made without departing from the inventive concept, it is not intended to limit the invention otherwise than as required by the appended claims.

What is claimed is:

1. An assembly for use in removing excessive ear wax from a patient's ear canal, said assembly comprising:

a) a speculum having a funnel which is adapted for insertion into the patient's ear canal; and b) an ear wax repository which is operably connected to said speculum in a manner wherein the position of the repository relative to the patient's ear canal is governed by the position of the speculum relative to the patient's ear canal, said repository being laterally offset from said speculum funnel, and being operative to receive ear wax from a tool that is used to dislodge ear wax from the ear canal.

2. The assembly of claim 1 wherein said ear wax repository is a cavity that is connected to said speculum, said cavity including a rim for scraping ear wax off of the tool and into the cavity.

3. The assembly of claim 2 wherein said cavity is formed integrally and in one piece with said speculum.

4. The assembly of claim 2 wherein said cavity is formed on a collar member which is removably connected to said speculum.

5. The assembly of claim 4 wherein said collar member includes an opening therein which allows said assembly to be suspended from the patient's ear during the ear wax removal procedure.

6. The assembly of claim 2 wherein said cavity rim is provided with a plurality of grooves operable to engage the ear wax removal tool, said grooves being operable to scrape ear wax off of the tool, and deposit the scraped ear wax in said cavity, when the tool is pulled through any of said grooves.

7. The assembly of claim 1 wherein said repository is a removable sheet of material onto which ear wax can be wiped from the ear wax removal tool.

8. The assembly of claim 7 wherein said sheet of material is in direct contact with said speculum.

9. The assembly of claim 7 wherein said sheet of material is removably connected to said speculum by means of a releasable clip.

10. The assembly of claim 7 wherein said sheet of material is removably connected to said speculum by means of a releasable hook.

11. The assembly of claim 1 wherein said repository is a suction tube extending into an interior portion of said speculum.

12. An assembly for use in removing excessive ear wax from a patient's ear canal, said assembly comprising:

a) a speculum having a funnel which is adapted for insertion into the patient's ear canal; and b) an ear wax repository cavity which is operably connected to said speculum in a manner wherein the position of the repository cavity relative to the patient's ear canal is governed by the position of the speculum relative to the patient's ear canal, said repository cavity being laterally offset from said speculum funnel, and being operative to receive ear wax from a tool that is used to dislodge ear wax from the ear canal.

13. The assembly of claim 12 wherein said ear wax repository cavity includes a rim for scraping ear wax off of the tool and into the ear wax repository cavity.

14. The assembly of claim 12 wherein said ear wax repository cavity is formed integrally and in one piece with said speculum.

15. The assembly of claim 12 wherein said ear wax repository cavity is formed on a collar member which is removably connected to said speculum.

16. The assembly of claim 15 wherein said collar member includes an opening therein which allows said assembly to be suspended from the patient's ear during the ear wax removal procedure.

17. The assembly of claim 12 wherein said ear wax repository cavity rim is provided with a plurality of grooves operable to engage the ear wax removal tool, said grooves being operable to scrape ear wax off of the tool, and deposit the scraped ear wax in said ear wax repository cavity, when the tool is pulled through any of said grooves.

18. An assembly for use in removing excessive ear wax from a patient's ear canal, said assembly comprising:

a) a speculum having a funnel which is adapted for insertion into the patient's ear canal; and b) an ear wax repository sheet which is removably connected to said speculum in a manner wherein the position of the ear wax repository sheet relative to the patient's ear canal is governed by the position of the speculum relative to the patient's ear canal, said ear wax repository sheet being laterally offset from said speculum funnel, and being operative to receive ear wax from a tool that is used to dislodge ear wax from the ear canal.

19. The assembly of claim 18 wherein said ear wax repository sheet is in direct contact with said speculum.

20. The assembly of claim 18 wherein said ear wax repository sheet is removably connected to said speculum by means of a releasable clip.

21. The assembly of claim 18 wherein said ear wax repository sheet is removably connected to said speculum by means of a releasable hook.

22. An assembly for use in removing excessive ear wax from a patient's ear canal, said assembly comprising:

a) a speculum having a funnel which is adapted for insertion into the patient's ear canal; and b) an ear wax repository which is operably connected to said speculum in a manner wherein the position of the repository relative to the patient's ear canal is governed by the position of the speculum relative to the patient's ear canal, said repository being disposed in said speculum funnel and said repository being a suction device that is operative to receive ear wax from a tool that is used to dislodge ear wax from the ear canal.

23. The assembly of claim 22 wherein said suction device is a tube which enters an interior portion of said speculum through a side wall of said speculum.

* * * * *